United States Patent [19]

Ruhl, Jr. et al.

[11] Patent Number: 5,134,291

[45] Date of Patent: Jul. 28, 1992

[54] METHOD FOR SORTING USED PLASTIC CONTAINERS AND THE LIKE

[75] Inventors: Harry D. Ruhl, Jr.; Kenneth R. Beebe, both of Midland, Mich.

[73] Assignee: The Dow Chemical Company, Midland, Mich.

[21] Appl. No.: 693,754

[22] Filed: Apr. 30, 1991

[51] Int. Cl.$^5$ .......................... G01J 1/00; B07C 5/342
[52] U.S. Cl. ..................... 250/341; 209/587; 250/340
[58] Field of Search ............. 250/340, 341, 339; 356/51; 209/577, 587

[56] References Cited

U.S. PATENT DOCUMENTS 3,747,755 7/1973 Senturia ........................ 250/339
4,915,827 4/1990 Rosenthal ....................... 209/577

OTHER PUBLICATIONS

L. G. Weyer, Utilizing Zero Crossover Points in the Near Infrared Reflectance Analysis of Industrial Polymers, *Journal of Applied Polymer Science*, 31, 2417–31 (1986).
E. W. Crandall, et al., *Journal of Applied Polymer Science*, 21, 449–454 (1977).
A. Giammarise, Near-Infrared Analysis of the Styrene Content of Copolymers with Aliphatic Acrylates and Methacrylates, *Analytical Letters*, 2(3), 117–121 (1969).
Plastic Recycling in Europe, Spring 1989, 28–29 and 58–59 and 67, Warren Spring Laboratory, Hertfordshire, Great Britain.
H. Kumasaki, et al., Selection of Polychlorinated Plastics in Plastic Waste by X-Ray Fluorescence Methods, *Intl. Journal of Applied Radiation and Isotopes*, 30, 637–642 (1979).
H. E. Howell and J. R. Davis, Qualitative Identification of Polymeric Materials Using Near-IR Spectroscopy, *Polym. Mater. Sci. Eng.*, 64, 88–89 (Mar. 1991).

*Primary Examiner*—Janice A. Howell
*Assistant Examiner*—Richard Hanig
*Attorney, Agent, or Firm*—Timothy S. Stevens

[57] ABSTRACT

A method for sorting a plurality of diverse objects into groups, each such object being made predominately from at least polyethylene terephthalate and polystyrene and at least two of polyvinyl chloride, polyethylene and polypropylene, the groups consisting at least of objects of like type of polymer identified to be polyethylene terephthalate and polystyrene and at least two of polyvinyl chloride, polyethylene and polypropylene. The method includes three steps. The first step is to irradiate the objects to be sorted with near-infrared radiation. The second step is to measure the diffuse reflectance of the irradiated objects in the near-infrared region to identify the objects as to the type of polymer used to make them. The third step is to direct the objects to their respective groups according to the measurement and identification of the second step.

6 Claims, 1 Drawing Sheet

METHOD FOR SORTING USED PLASTIC CONTAINERS AND THE LIKE

BACKGROUND OF THE INVENTION

There is an increasing interest in recycling waste plastic objects such as used plastic containers. Generally, the recycling of such materials requires that they be sorted as to the type of plastic used to make them. Many plastic containers now have a symbol imprinted upon them identifying the type of plastic used to make them so that consumers or recycling plant operators can manually sort the containers for recycling. Automated sorting methods and apparatus have been developed for waste plastic materials based on various identification technologies such as infrared spectroscopy and X-ray fluorescence techniques.

Automated sorting methods and apparatus have been developed for agricultural products based on near-infrared absorption spectroscopy. Plastic materials have been identified as to whether they are linear polymers, e.g., polyethylene, or cyclic polymers, e.g., polystyrene, by near-infrared reflectance spectroscopy.

SUMMARY OF THE INVENTION

A method for sorting a plurality of diverse objects into groups, each such object being made predominately from at least polyethylene terephthalate and polystyrene and at least two of polyvinyl chloride, polyethylene and polypropylene, the groups consisting at least of objects of like type of polymer identified to be polyethylene terephthalate and polystyrene and at least two of polyvinyl chloride, polyethylene and polypropylene. The method includes three steps. The first step is to irradiate the objects to be sorted with near-infrared radiation. The second step is to measure the diffuse reflectance of the irradiated objects in the near-infrared region to identify the objects as to the type of polymer used to make them. The third step is to direct the objects to their respective groups according to the measurement and identification of the second step.

DETAILED DESCRIPTION OF THE INVENTION

Figure 1:
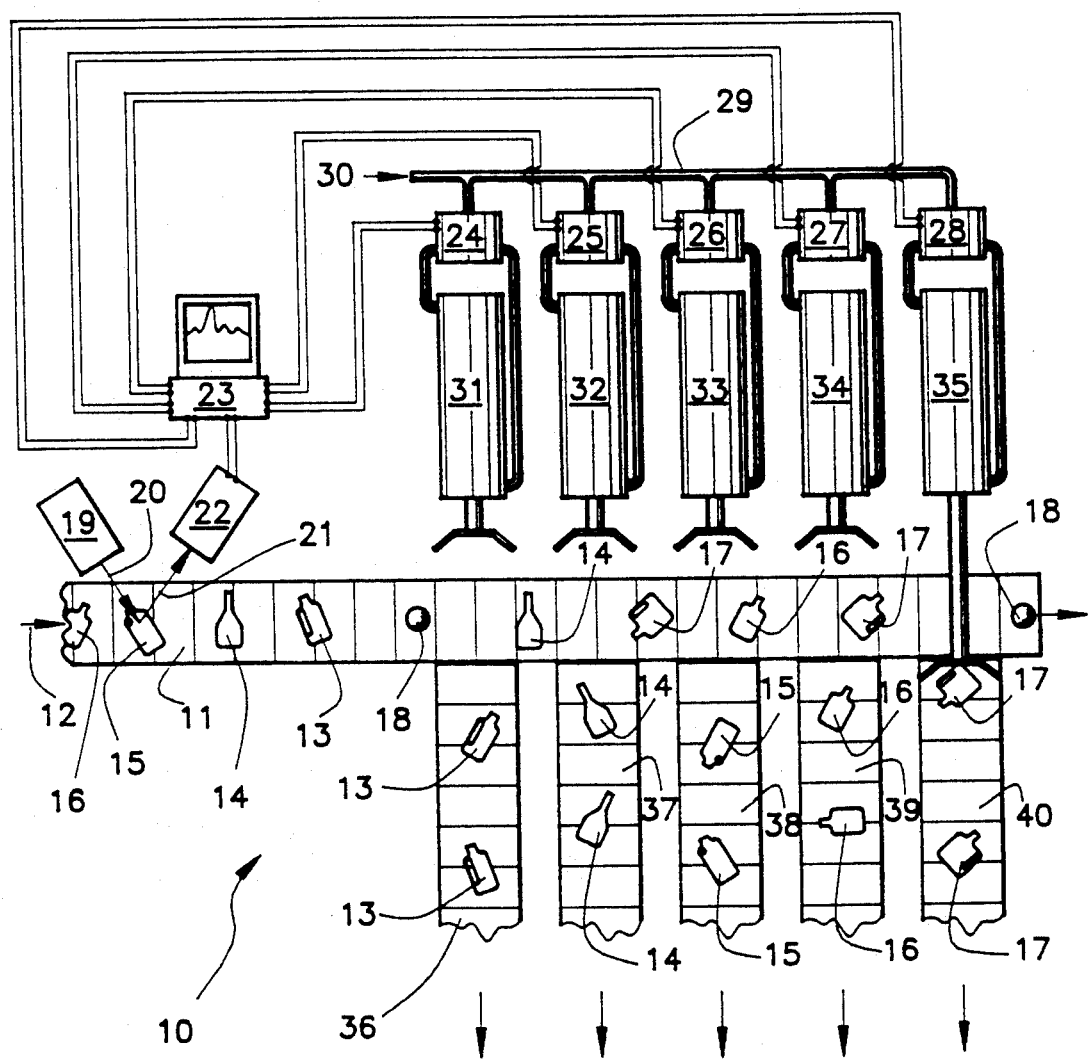
FIGURE 1 is an upper view of an apparatus that can be used to carry out the method of the invention.

Referring now to FIGURE 1, therein is shown an apparatus 10 that can be used to carry out the method of the invention which includes a conveyor 11 operated at constant speed in the direction of the arrows 12. Various waste plastic containers are disposed on the conveyor 11 including containers made respectively of polyethylene terephthalate 13, polyvinyl chloride 14, polyethylene 15, polypropylene 16, polystyrene 17 or unidentified objects 18. It is desired to sort the containers 13-17 into groups with each group consisting of objects being made of the same type of polymer. Although the objects to be sorted can be made of any material, e.g., metals, paper, plastics or any combination thereof, it is critical in that at least some of the objects be made predominately from polyethylene terephthalate and polystyrene as well as predominately from at least two of polyvinyl chloride, polyethylene and polypropylene. Thus, for example, objects including: an object made predominately from polyethylene terephthalate; an object made predominately from polystyrene; an object made predominately from polyvinyl chloride; and an object made predominately from polyethylene.

A source of near-infrared light 19 is used to shine a beam 20 of near-infrared light onto the conveyor 11. The source 19 is preferably an ordinary tungsten lamp. When a container 13-17 passes under the beam 20 the container 13-17 reflects near-infrared light 21 into a near-infrared light detector 22. The detector 22 can be a scanning grating near-infrared spectrometer but it is believed that a diode array near-infrared spectrometer is preferable because a diode array near-infrared spectrometer is capable of generating more spectra in a given time, thus allowing for more rapid sorting. The detector 22 is connected to a digital computer 23. The computer 23 is connected to a series of solenoid valves 24, 25, 26, 27 and 28. A manifold 29 is used to feed compressed air 30 to the valves 24, 25, 26, 27 and 28. The solenoid valves 24, 25, 26, 27 and 28 are used to control a series of air actuated pushers 31, 32, 33, 34 and 35. The computer 23 is programmed to identify the type of polymer of the container passing under the beam 20. Since the conveyor 11 is operated at constant speed, then the computer 23 can delay actuate the appropriate pusher 31, 32, 33, 34 or 35 to direct a container to its respective group via conveyors 36, 37, 38, 39 and 40 which are each operated in the direction shown by the arrows. As shown in FIGURE 1, the pusher 35 is pushing a container 17, identified to be polystyrene, onto the conveyor 40. If the computer 23 does not identify an object, then it is not pushed onto any of the conveyors 36, 37, 38, 39 or 40 and such an event is depicted in FIGURE 1 as an object 18 which will be directed to a group consisting of unidentified objects.

The computer 23 can, of course, be programmed in hardware or in software. The computer 23 can manipulate data in the form of discrete wavelength measurements and in the form of spectra. A measurement at one wavelength can be ratioed to a measurement at another wavelength, e.g., polyvinyl chloride can be differentiated from polyethylene terephthalate by ratioing the measurement at 1718 and 1668 cm$^{-1}$. Preferably, however, the data is manipulated in the form of spectra. It has been determined that the diffuse reflectance spectra for polyethylene terephthalate, polyvinyl chloride, polyethylene, polypropylene and polystyrene are different enough to allow for their identification in the invention. However, it is preferable to manipulate the spectra with the computer 23 to make these differences more apparent and the resulting identification more reliable. Preferably this is done by analog signal processing and digital pattern recognition. For example, the second derivative of the signal form the detector 22 normalized at 1600 cm$^{-1}$ is manipulated to determine at what wavelengths the second derivative either is positive or negative in excess of a set value. On this basis the following pattern recognitions can be made: polyethylene terephthalate, + at 1668 and − at 1665 cm$^{-1}$; polyvinyl chloride, + at 1717 and − at 1735 cm$^{-1}$; polystyrene, + at 1665, + at 1680 and − at 1743 cm$^{-1}$; polypropylene, + at 1687, + at 1697 and − at 1680 cm$^{-1}$; and polyethylene, + at 1730, + at 1735 and − at 1750 cm$^{-1}$ (and not polypropylene). There are a number of other combinations that could have been chosen, the above being one option. The success of this approach depends on having adequate spectral resolution and thus a filter photometer may not have adequate resolution. A similar approach could be taken using first derivatives of the spectra.

Another approach to treating the data is a K-nearest neighbor classification. Explaining how this works is best accomplished if the spectra are thought of as single points in multidimentional space. The more typical method of plotting a spectrum is to define the X axis as wavelength and the Y axis as absorbance. However, it is also possible to plot the spectra in multidimensional space. The first dimension is defined as wavelength 1, the second dimension as wavelength 2 and so forth for all n wavelengths. The position of a spectrum in this n dimensional "wavelength space" is determined by the absorbances at each wavelength. The following three-wavelength spectrum can be used to illustrate this point: absorbance at wavelength $1=1.4$; absorbance at wavelength $2=0.9$; and absorbance at wavelength $3=1.9$. The plot of this spectrum would be a single point in 3 dimensional space and the position of the spectrum would be at the coordinate $X=1.4$, $Y=0.9$ and $Z=1.9$. This approach can be extended to spectra with more than three wavelengths so that a spectrum with 20 wavelengths would be a point in 20 dimensional space. It is not possible to graphically represent this spectrum, but the concept can be understood as a simple extension of the three dimensional example and, of course, digital computers can easily be programmed to operate in n dimensions.

Carrying this example a bit further, if a hypothetical noise-free situation is considered where two spectra have identical absorbances at 20 wavelengths, the two spectra would have the same position in a 20 dimensional wavelength space. On the other hand, nonidentical spectra would have different positions in this space. In K-nearest neighbor classification, the distance between spectra is used as a measure of similarity and difference. Spectra that are close to each other are labeled "similar" while distant points are treated as "dissimilar". To perform a K-nearest neighbor classification the analyst must first decide on the measure to use for distance and the number of neighbors to use for classification (K), for example, the Euclidean distance and a two nearest neighbor rule.

Given the spectra of a set of samples representing the different types of plastics, the performance of the K-nearest neighbor rule can be treated in the following manner. First, the euclidean distance is calculated between sample 1 and each of the remaining spectra. Next, the two smallest distances are used to identify the two nearest neighbors and classify the sample. For example, if both neighbors are polyethylene samples, the sample would be classified as polyethylene with a probability of 100%. If one of the nearest neighbors is polyethylene and the other polystyrene, then the sample would be given a probability of 50% for being either polyethylene or polystyrene. This process is repeated for each of the samples so that the predictive ability of the method is tested on each sample.

K-nearest neighbor classification is only one of the many different approaches that can be used to identify samples. Other approaches, e.g., discriminate analysis, can be employed if certain assumptions can be made regarding the data. The K-nearest neighbor approach is preferably used in the spectral region between 1500 and 1800 cm$^{-1}$. Preferably, the spectra are normalized by dividing the amplitude at each wavelength by the square root of the sum of the squares for all wavelengths.

What is claimed is:

1. A method for sorting a plurality of diverse objects into groups, each such object being made predominately from at least polyethylene terephthalate and polystyrene and at least two of polyvinyl chloride, polyethylene and polypropylene, the groups consisting at least of objects of like type of polymer identified to be polyethylene terephthalate and polystyrene and at least two of polyvinyl chloride, polyethylene and polypropylene, the method comprising the steps of:

(a) irradiating the objects to be sorted with near-infrared radiation;
    (b) measuring the diffuse reflectance of the irradiated objects in the near-infrared region to identify the objects as to the type of polymer used to make them;
    (c) directing the objects to their respective groups according to the measurement and identification of step (b).

2. The method of claim 1 wherein in step (b) a first derivative is made of a diffuse reflectance spectra of the objects in the near-infrared region.

3. The method of claim 1 wherein in step (b) a second derivative is made of a diffuse reflectance spectra of the objects in the near-infrared region.

4. The method of claim 1 wherein in step (b) at least one ratio is made of the diffuse reflectance measurement at at least two different wavelengths in the near-infrared region.

5. The method of claim 1 wherein in step (b) a diffuse reflectance spectra of the objects in the near-infrared region is positioned in multidimensional space using a digital computer.

6. The method of claim 1 wherein in step (b) a photodiode array detector is used to measure the diffuse reflectance of the objects in the near-infrared region.

* * * * *